United States Patent [19]
Werne

[11] Patent Number: 5,744,958
[45] Date of Patent: Apr. 28, 1998

[54] INSTRUMENT HAVING ULTRA-THIN CONDUCTIVE COATING AND METHOD FOR MAGNETIC RESONANCE IMAGING OF SUCH INSTRUMENT

[75] Inventor: Roger W. Werne, San Ramon, Calif.

[73] Assignee: ITI Medical Technologies, Inc., Livermore, Calif.

[21] Appl. No.: 554,446

[22] Filed: Nov. 7, 1995

[51] Int. Cl.$^6$ ..................................................... G01V 3/00
[52] U.S. Cl. ........................................ 324/318; 128/653.2
[58] Field of Search .................................. 324/318, 322, 324/300, 307, 321, 301, 309; 128/653.2–653.5

[56] References Cited

U.S. PATENT DOCUMENTS

| | | | |
|---|---|---|---|
| 4,572,198 | 2/1986 | Codrington | 128/653 |
| 4,827,931 | 5/1989 | Longmore | 128/334 R |
| 4,984,573 | 1/1991 | Leunbach | 128/653 |
| 4,989,608 | 2/1991 | Ratner | 128/653 A |
| 5,154,179 | 10/1992 | Ratner | 128/653.4 |
| 5,155,435 | 10/1992 | Kaufman et al. | 324/309 |
| 5,188,111 | 2/1993 | Yates et al. | 128/657 |
| 5,201,314 | 4/1993 | Bosley et al. | 128/662.02 |
| 5,211,166 | 5/1993 | Sepponen | 128/653.5 |
| 5,218,964 | 6/1993 | Sepponen | 128/653.2 |
| 5,262,727 | 11/1993 | Behbin et al. | 324/318 |
| 5,271,400 | 12/1993 | Dumoulin et al. | 128/653.2 |
| 5,290,266 | 3/1994 | Rohling et al. | 604/272 |
| 5,318,025 | 6/1994 | Dumoulin et al. | 128/653.2 |
| 5,353,795 | 10/1994 | Souza et al. | 128/653.2 |
| 5,357,958 | 10/1994 | Kaufman | 128/653.2 |
| 5,409,003 | 4/1995 | Young | 128/653.2 |
| 5,419,325 | 5/1995 | Dumoulin et al. | 128/653.2 |
| 5,534,778 | 7/1996 | Loos et al. | 324/318 |

FOREIGN PATENT DOCUMENTS

| | | | |
|---|---|---|---|
| 0 165 742 | 12/1985 | European Pat. Off. | A61M 25/00 |
| WO 87/04080 | 7/1987 | WIPO | A61M 25/00 |

OTHER PUBLICATIONS

Jolesz, et al., "Interventional Use of Magnetic Resonance Imaging," Magnetic Resonance Quarterly, vol. 10, No. 2, pp. 85–96 (1994).

Bunshah, et al., *Deposition Technologies for Films and Coatings*, Noyes Publications, Park Ridge, New Jersey, pp. 85 and 170–172 (1982).

*Primary Examiner*—Louis M. Arana
*Attorney, Agent, or Firm*—Limbach & Limbach L.L.P.

[57] ABSTRACT

A coated instrument for use in a magnetic resonance imaging (MRI) system, a method for designing such an instrument, and an MRI method including the steps of positioning a coated instrument (constructed in accordance with the invention) and a target in the imaging region of an MRI system, and operating the MRI system to produce an image showing both the target and the instrument. The instrument has a non-electrically conductive body covered by an electrically conductive, ultra-thin coating on at least part of the body. The thickness of the coating is determined (preferably experimentally) to be just large enough to cause the instrument to be positively shown in an MR image produced by the MRI system, but not so large as to obscure or distort unacceptably the image of a target (e.g., a typical target, such as human tissue, with which the instrument is to be imaged) in the same MR image (where both the instrument and target are in the MRI system's imaging region when the MRI system produces the MR image). The ultra-thin coating actually creates an imaging artifact which is sufficient to cause the instrument to be visible, but not so significant as to unacceptably distort the image of the intended target. In some preferred embodiments, the coating is a metal whose thickness is 2000 Angstroms or less. In other preferred embodiments, the coating is a metal whose thickness is of the same order of magnitude as its skin depth with respect to the radio frequency (RF) of the MRI system's RF field.

17 Claims, 2 Drawing Sheets

INSTRUMENT HAVING ULTRA-THIN CONDUCTIVE COATING AND METHOD FOR MAGNETIC RESONANCE IMAGING OF SUCH INSTRUMENT

FIELD OF THE INVENTION

The invention pertains to use of magnetic resonance imaging ("MRI") in applications, such as medical therapy, in which a target (e.g., a human patient or animal) and an instrument (e.g., a catheter or biopsy needle) are present within the field of view of an MRI system. In preferred embodiments, the invention is an instrument whose structure enables it to be visualized by an MRI system without displacing and/or distorting or degrading the image of the target also being imaged by the MRI system, and a method for using such instrument.

BACKGROUND OF THE INVENTION

Magnetic resonance imaging ("MRI") systems are in widespread use for medical diagnostics. However, new applications including therapy, as well as other applications are being developed. During magnetic resonance imaging, an MRI system generates a strong magnetic field. When a target object (containing water molecules or other hydrogenous compounds) is positioned in the field, the field aligns magnetic dipoles of the hydrogen nuclei within the water molecules (and other hydrogen atoms), as explained for example in Morris, Peter G., *Nuclear Magnetic Resonance Imaging in Medicine and Biology*, Clarendon, Oxford, 1986. The magnetic field strength required to so align the magnetic dipoles is typically on the order of one Tesla, but field strengths significantly higher and lower than one Tesla are also used in various applications of MRI. The magnetic field imparts a resonant frequency to the nuclei that is proportional to the field strength. Once aligned by the magnetic field, the magnetic dipoles can be rotated out of alignment by application of radio frequency (RF) energy at the resonant frequency of the system. Electromagnetic radiation is subsequently emitted by the resonating magnetic dipoles (i.e., the protons spinning at their resonance frequency), as they return to alignment with the field. Imaging occurs as a result of detecting such radiation emitted from each of many different regions within the target.

In medical diagnosis using MRI, the target is all or part of a human patient or animal positioned in the imaging region of an MRI system (where "imaging region" denotes the space within an MRI system in which a target can be imaged), and the MRI system produces an image of one or more selected portions of the patient.

Medical therapy performed on a patient while the patient is being imaged using MRI is sometimes referred to as interventional magnetic resonance or magnetic resonance therapy ("MRT"), as explained in Jolesz, Ferenc A., Blumenfeld, Morry S., "Interventional Use of Magnetic Resonance Imaging," Magnetic Resonance Quarterly, Vol. 10, No. 2, pp. 85–96 (Jolesz, et al.). In MRT, the patient and at least one instrument necessary to perform a therapeutic function, are positioned in the imaging region of an MRI system. Examples of instruments used in MRT are scalpels, forceps, retractors, biopsy needles, catheters, and the like. Implanted devices used for therapy such as sutures, pacemakers, stents, shunts, orthopaedic devices, dental devices and the like are also examples of such instruments. It is typically desired that the MRT system portray one or more of the instruments while also imaging a selected portion of the patient. For example, it may be desirable to visualize a biopsy needle or catheter inserted in the tissue of the patient. In addition, it is also desirable to have permanently implanted medical devices such as blood filters, stents, or other such implants visualized in the MR image without affecting the image quality of the surrounding tissue structures.

In addition to such medical applications of MRI, it may also be commercially or scientifically useful to employ a tool (not necessarily a medical instrument) to perform an operation (other than medical therapy) on a target (not necessarily a human patient) in the imaging region of an MRI system, while the MRI system images show both the target and the tool during the operation.

Throughout this specification, including in the claims, the term "instrument" is used in a broad sense to denote any tool, instrument, or other object employed to perform (or useful for performing) an operation (such as but not limited to medical therapy) on a target, or a device which is implanted in the body for some therapeutic reason or purpose. Any such instrument appears on the target images produced by the MRI system, if the instrument embodies the invention. The term "target" denotes any object to be imaged by the MRI system (such as but not limited to a human patient). Typically, the structure of a "target" is not specially designed or altered to enhance or optimize visibility when imaged by an MRI system. In contrast, the structure of the inventive "instrument" is specially designed for optimal visibility on MR images.

Throughout this specification, including in the claims, the expression "MR image" denotes a magnetic resonance image (typically displayed on a display device such as a cathode ray tube or flat panel display) generated by an MRI system of whatever object is (or whatever objects are) present in a selected cross-section of its imaging region.

To appreciate one important class of medical uses of instruments designed in accordance with the invention, it is helpful to consider the following background considerations. One of the most promising opportunities for cost reduction in the medical field is more widespread use of image guided "minimally invasive" therapy. The term "minimally invasive" refers to the fact that the patient is not traumatized by radical surgical openings to access diseased tissue. Conventional invasive surgery is typically associated with a higher risk of complications than is minimally invasive surgery, and usually requires longer periods of hospitalization than does minimally invasive surgery.

One of the most promising imaging modalities for minimally invasive therapy is magnetic resonance imaging ("MRI"). This is because MRI gives superior soft tissue contrast that clearly images important anatomical features, allowing identification of normal versus abnormal tissue structures.

Principal manufacturers of MRI equipment have developed new generations of high-speed MRI systems which permit continuous, real time visualization of tissue during surgical and endovascular procedures. Such recently developed MRI systems also provide better access to the patient. In one recently developed class of MRI systems, the patient is suspended on a platform between two large, doughnut-shaped magnets. With a magnetic field set up between the magnets, real time images ("MR images") are produced on a monitor above the patient. This provides a surgeon with physical access to the patient, and enables the surgeon to perform a procedure on the patient while viewing the internal tissue structures which are the object of the procedure on the monitor in real time. As MRI technology develops, the clarity, definition, and variety of images available to surgeons are expected to improve significantly (as discussed in Jolesz, et al.).

In magnetic resonance therapy ("MRT"), the presence of both the magnetic and RF fields used in the imaging process place several constraints on each instrument to be positioned or manipulated near or in the imaging region of an MRI system, including the following:

1. the instrument must be essentially non-ferromagnetic, so that it is not attracted by magnetic field (such attraction would create a safety problem). This consideration applies to any object which is implanted within the patient being imaged, because the magnetic field would subject such an implant to undesirable forces and torque's if it were made entirely of ferromagnetic material;

2. an electrical instrument must be tolerant of the static and pulsed magnetic and RF fields, in the sense that it can function in the presence of these fields;

3. a metallic implant or other metallic instrument should not be subject to significant induction heating due to the applied RF field; and 4. the instrument should not create imaging artifacts that obscure or distort the image of the target.

Because of these constraints, instruments used in MRT operations have conventionally been made of non-ferromagnetic metal such as titanium, nitinol, some types of stainless steel, aluminum, copper, or brass. However, such non-ferromagnetic metal instruments have the following undesirable imaging property when imaged together with a human patient in an MRI system. The non-ferromagnetic metal instruments, just as most non-hydrogenous materials, will be "negatively" imaged by the MRI system as a black void in a positive background (a "sea" of gray shaded tissue structures). The instrument displaces tissue that normally would be imaged. In areas where the patient's tissue structure has a dark gray or black appearance (due to a weak or absent radiation signal from the magnetic dipoles of its water molecules), the negative image (void) created by the instrument is insufficient for visualization. Also, metallic, non-ferromagnetic materials (unless they are ultra-thin) may cause unacceptable imaging artifacts when imaged by an MRI system. Such artifacts (which can have the appearance of a halo or glow around the material which would obscure or distort the image of any target material) occur because the presence of the RF field sets up eddy currents in the non-ferromagnetic material, which in turn create inhomogeneities in the magnetic field of the MRI system. In addition, imaging artifacts are caused by incompatibilities in the magnetic susceptibilities of materials that are in the imaging field.

It would be desirable to design an instrument for use in an MRI system to be "MR visible," in the sense that the instrument would have its own identifiable magnetic resonance signal (and thus be positively imaged) in the presence of the combined magnetic and RF fields of the MRI system.

There have been attempts to design such an "MR visible" instrument. For example, U.S. Pat. No. 4,989,608, issued Feb. 5, 1991 to Ratner, and U.S. Pat. No. 5,154,179, issued Oct. 13, 1992 to Ratner, disclose catheters which are intended to be MR visible. In some embodiments, the catheters are composed of plastic, and ferromagnetic particles are distributed uniformly throughout the volume of each catheter or in patterned regions within each catheter's volume (e.g., in stripes along each catheter's longitudinal axis). In other embodiments, the catheters include internal chambers filled with liquid (containing aqueous paramagnetic ions). A disadvantage of the Ratner method is that the ferromagnetic particles or aqueous paramagnetic ions must be immersed in a carrier volume of material. This carrier volume must be either the volume of the plastic catheter material itself or a liquid volume which is inserted in a catheter lumen.

U.S. Pat. Nos. 4,989,608 and 5,154,179 also teach that "non-ferrous materials" can be included in a catheter containing ferromagnetic particles or a volume of aqueous paramagnetic ions, so that the catheter is visible under X-rays (in addition to being MR visible), and they teach that the nonferrous materials should be "small" to minimize the artifacts they may generate in both magnetic resonance and X-ray images. However, these references do not suggest coating an instrument with an electrically conductive coating to make the instrument MR visible, or coating an instrument with an electrically conductive coating whose thickness is chosen to cause the instrument to create just enough artifact to be visible in an MRI system, but not so much artifact as to significantly degrade the magnetic resonance imaging of a target (e.g., human tissue) being imaged (with the instrument) by the MRI system.

The present invention is based on the inventor's recognition that an electrically conductive, "ultra-thin" coating (a coating whose thickness is less than or of the same order of magnitude as the coating's skin depth with respect to its electrical and magnetic properties and the frequency of the RF field in an MRI system) on an instrument can cause the instrument to create just enough artifact to be visible when imaged by an MRI system, but not so much artifact as to obscure or distort unacceptably the magnetic resonance imaging of a target (e.g., human tissue) also being imaged by the MRI system. In other words, the invention controls the artifact in such a way as to make the instrument visible but not appreciably distort the tissue structures being imaged by the MRI. An ultra-thin coating on an instrument embodying the invention typically has a thickness of on the order of hundreds or thousands of Angstroms.

SUMMARY OF THE INVENTION

In a class of embodiments, the invention is a coated instrument for use in an MRI system. The instrument has a non-electrically conductive body, and an electrically conductive, ultra-thin coating on at least part of the body. The coating can be a ferromagnetic metal or non-ferromagnetic metal. Also preferably, the thickness of the coating is determined experimentally to be just large enough to cause the instrument to be positively visualized in an MR image produced by an MRI system, but not so large as to obscure or distort unacceptably the image of a target (e.g., a typical target, such as human tissue, adjacent to the instrument) in any of the target's MR images (where both the instrument and target are in the MRI system's imaging region when the MRI system produces MR images).

In some preferred embodiments, the coating is a non-ferromagnetic metal (such as gold) whose thickness is at least substantially equal to 2000 Angstroms. In other preferred embodiments, the coating is a non-ferromagnetic metal whose thickness is less than (or of the same order of magnitude as) its skin depth with respect to RF electromagnetic radiation at the MRI system's RF frequency.

Another aspect of the invention is a magnetic resonance imaging method including the steps of positioning both a coated instrument (constructed in accordance with the invention) and a target in the imaging region of an MRI system, and operating the system to produce an MR image showing both the target and the instrument.

DETAILED DESCRIPTION OF THE PREFERRED EMBODIMENTS

Figure 1:
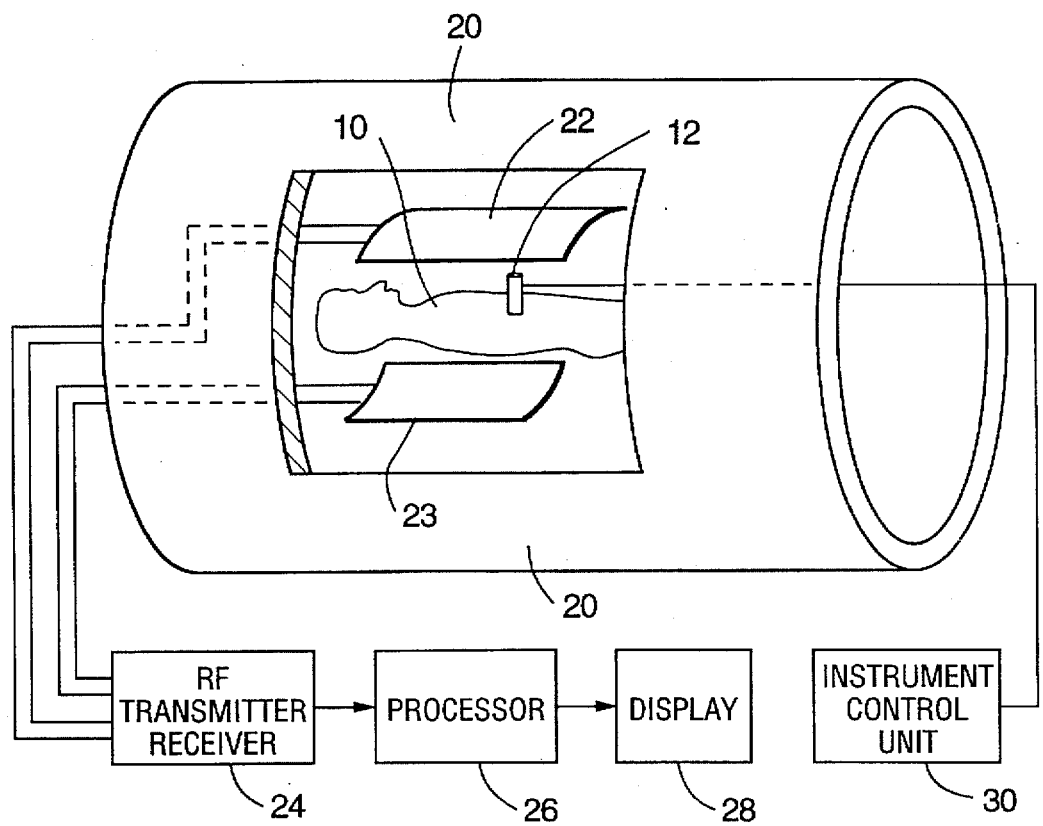
FIG. 1 is a simplified schematic diagram of an MRI system with an embodiment of the coated instrument of the invention, and a target, in its imaging region.

The MRI system shown in FIG. 1 can be operated to implement the magnetic resonance imaging method of the invention. With reference to FIG. 1, cylindrical magnet structure 20 includes magnets for producing a magnetic field suitable for magnetic resonance imaging of target 10. A portion of structure 20 is cut away in FIG. 1 to show both target 10 and coated instrument 12 positioned in an imaging region which lies between coils 22 and 23 and is surrounded radially by structure 20. An RF transmitter within RF transmitter/receiver 24 supplies an appropriate electric signal to coils 22 and 23 to cause an RF magnetic field to be superimposed with the magnetic field (due to magnet structure) in the imaging region. The superimposed magnetic and RF fields causes magnetic dipoles of target 10 to resonate. An RF receiver within transmitter/receiver 24 detects electromagnetic radiation that has propagated from the resonating magnetic dipoles to coils 22 and 23. Unit 24 supplies signals indicative of the detected radiation to processor 26 (preferably a programmed digital computer), and processor 26 processes these signals to generate display data (for determining an MR image) and supplies the display data to display device 28 (which can be a conventional cathode ray tube or flat panel display device). In response to the display data, an MR image of a selected cross-sectional portion of target 10, or a selected cross-sectional portion of target 10 including instrument 12, is displayed on display device 28.

In preferred embodiments, target 10 is a human patient or animal and instrument 12 is a medical device such as a scalpel, forceps, retractor, biopsy needle, catheter, or the like.

While viewing the MR image on display device 28, a medical practitioner can manipulate instrument 12. The practitioner may accomplish this manipulation manually (e.g., by gripping and moving the instrument). Alternatively, instrument 12 can be manipulated remotely in response to instrument control signals which are generated by instrument control unit 30 (in response to a medical practitioner's actuation of controls of unit 30) and supplied to from unit 30 to instrument 12.

Figure 2:
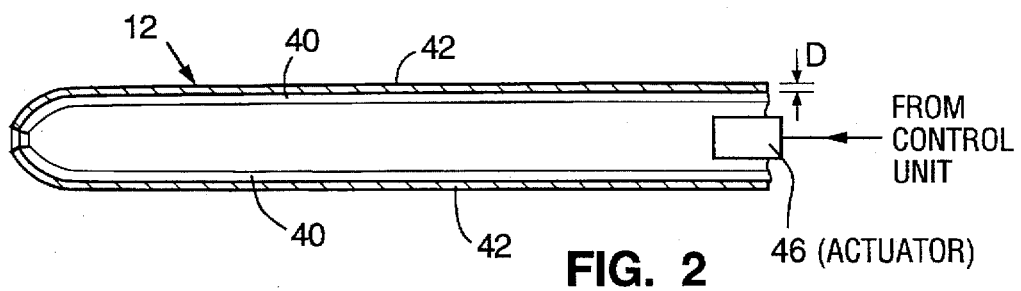
FIG. 2 is an enlarged, simplified cross-sectional view of the coated instrument shown in FIG. 1.

As shown in FIG. 2, instrument 12 can be a hollow needle-shaped device, including a generally cylindrical body 40 (composed of non-electrically conductive material such as ceramic material, fiber composite, plastic or rubber), an ultra-thin coating 42 (composed of electrically conductive material) on body 40, and optionally also an actuator 46 (or another means for implementing an operation in response to remotely generated control signals, such as control signals received from unit 30 of FIG. 1). Actuator 46 functions by moving instrument 12, or a component of instrument 12, relative to target 10 in response to control signals from unit 30.

Preferably, coating 42 consists of non-ferromagnetic metal (such as gold, silver, or platinum) deposited on body 40. Alternatively, coating 42 can consist of any other metal, including a ferromagnetic material if it is sufficiently thin so as not to cause significant forces and torques to develop on the instrument.

Figure 3:
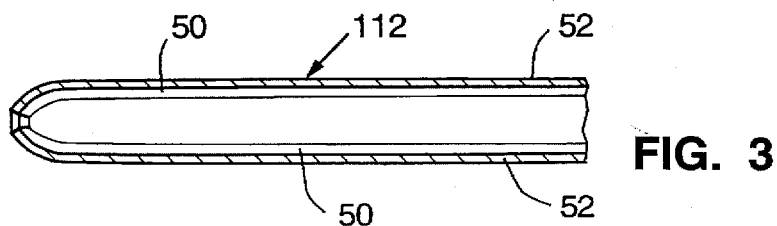
FIG. 3 is a simplified cross-sectional view of another embodiment of the coated instrument of the invention.
Figure 5A:
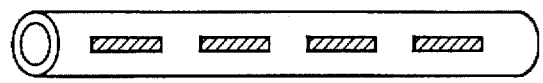
FIGS. 5(a), 5(b), 5(c), 5(d), 5(e), and 5(f) are examples of instruments having different coating patterns that are used in alternative embodiments of the instrument of the invention. (In those patterns consisting of discrete elements, such as that of FIG. 5(c), each element can have a different thickness, although all the elements should be ultra-thin.)
Figure 5B:
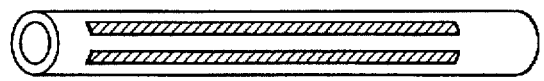
Figure 5C:
Figure 5D:
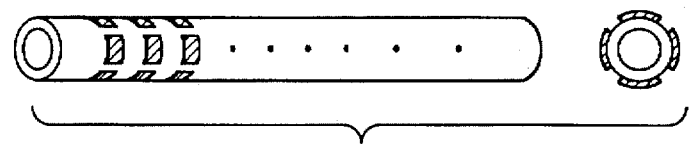
Figure 5E:
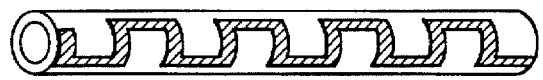
Figure 5F:

Another embodiment of the inventive coated instrument of the invention is instrument 112 shown in FIG. 3. Instrument 112 differs from above-described instrument 12 primarily in that instrument 112 includes no means (such as actuator 46 of instrument 12) for implementing an operation in response to remotely generated control signals. As shown in FIG. 3, instrument 112 is a hollow needle-shaped device, including a generally cylindrical body 50 (composed of non-electrically conductive material such as ceramic material, plastic, fiber composite or rubber), and an ultra-thin coating 52 (composed of electrically conductive material) on body 50.

Figure 4:
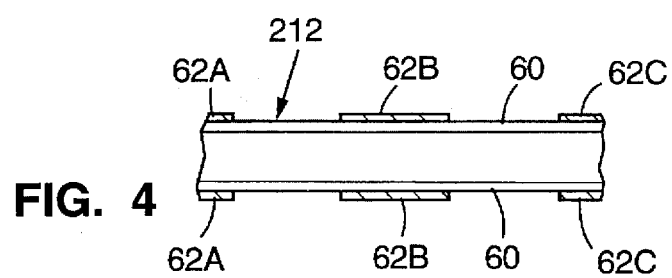
FIG. 4 is a simplified, partial cross-sectional view of another embodiment of the coated instrument of the invention.

In another class of embodiments, the instrument of the invention includes a body and an ultra-thin conductive coating that covers a patterned region of the body (but not the entire body). Instrument 212 of FIG. 4 is an example of an instrument in this class of embodiments. Instrument 212 consists of body 60 (composed of non-electrically conductive material such as ceramic material, plastic, fiber composite or rubber), and an ultra-thin coating (composed of electrically conductive material) on body 60. The portion of body 60 shown in FIG. 4 is hollow and generally cylindrical, and the ultra-thin coating is deposited on annular regions 62A, 622, and 62C of the outer surface of body 60.

In another class of embodiments, instrument 212 has any of a variety of patterns of ultra-thin conductive material designed to further enhance and control the visibility of instrument 212. The geometry of such patterns needed to control the visibility may be dependent on the surface geometry of instrument 212 and on the polarization of the RF waves used to generate the MR signal in the target body 10. It is possible that it may be desirable for the ultra-thin coatings on annular regions 62A, 62B and 62C of the outer surface of body 60 to all be of the same thickness (as shown in FIG. 4) or of differing thicknesses so that the instrument could be visible under a broader range of MRI machine conditions. Examples of instruments with such coating are shown in FIGS. 5(a)–5(f). In those patterns consisting of discrete elements (such as that of FIG. 5(a) or FIG. 5(c)), each element can have a different thickness, but all the elements should be ultra-thin.

In preferred embodiments of the coated instrument of the invention, the thickness of the conductive coating (e.g., thickness D of coating 42 of instrument 12 of FIG. 2) is determined experimentally, in the following manner. An MRI system images the instrument several times, together with a target (preferably with a typical target such as a MR phantom), each time with a conductive coating having a different thickness. The coating thickness which satisfies the following criteria is identified as the preferred thickness: the coating should be thick enough to cause the instrument to be positively shown by the MRI system, and the coating should not be so thick as to cause the instrument to unacceptably distort or obscure the image of the target produced by the same MRI system. The instrument is "positively shown" by the MRI system if a representation of the instrument (which approximates closely the instrument's real shape) is visible in an MR image generated by the system, other than as a black or "negative" void in a positive background of gray shaded or colored features. For example, an instrument is "positively shown" by an MRI system if a gray outline of the instrument's coated outer surface (or a gray shaded region bounded by such an outline) appears in an MR image, together with (but distinguishable from) a gray shaded representation of features of a target.

The verb "degrade" (or another form of this verb) will sometimes be used herein, including in the claims, to refer collectively to the corresponding form of the verbs "distort" and "obscure."

The inventor has obtained experimental data comprising MR images of a body of silica glass (of dimensions 1.0 inch by 1.0 inch by 0.125 inch) in the imaging (combined magnetic and RF) field of a 2.0 Tesla MRI system, with various ultra-thin metal coatings on such silica glass body. The data established that the system could generate an MR image that positively showed the glass body when a gold coating (of thickness 2000 Angstroms) covered the body. Neither a coating of niobium (of thickness 400 Angstroms), nor a coating of titanium (of thickness 1000 Angstroms) covering the body, resulted in an MR image that positively showed the coated body in this experiment.

In preferred embodiments, the thickness of the conductive coating on the inventive instrument (e.g., thickness D of coating 42 of instrument 12 of FIG. 2) is 2000 Angstroms.

In all embodiments, the thickness of the "ultra-thin" conductive coating on the inventive instrument (e.g., thickness D of coating 42 of instrument 12 of FIG. 2) is less than, or of the same order of magnitude as, the "skin depth" of the coating material with respect to the RF frequency of the MRI system (e.g., that of the RF field produced in the FIG. 1 system by coils 22 & 23 in response to the RF transmitter in unit 24). The following explanation of the concept of "skin depth" should be helpful in appreciating the advantages of these embodiments.

When electromagnetic waves having frequency in the RF (radio frequency) range impinge on an electrical conductor, at least some of the waves are absorbed by the conductor, and such waves will propagate in the conductor at a speed and frequency determined by the wave itself, the material properties of the conductor, and Maxwell's equations of electromagnetism. These equations dictate that the resulting current flow in the conductor will occur as a surface wave in the conductor; not as a current uniformly distributed across the conductor's cross-section. This surface wave phenomenon dictates that the field strength in the conductor decreases exponentially from its maximum at the conductor's surface (the surface at which the radiation is incident). The "skin depth" as it is defined herein, is the depth of penetration ("d") in the conductor at which the field strength has decayed to 1% of its maximum value at the surface, and is given by:

$$d=4.6(\rho f \mu \sigma)^{-\frac{1}{2}},$$

where $\pi=3.14159\ldots$, f=the frequency of the field in the conductor, $\mu$=the permeability of the conductor, and a $\sigma$=the electrical conductivity of the conductor In this application, the term "ultra-thin coating" refers to a coating whose thickness is of the order of the skin depth of the material or less.

By varying the thickness of an ultra-thin conductive coating on a non-conductive substrate (body) before allowing electromagnetic radiation to be incident at the coating, the amount of electrical energy absorbed in the coating and the amount of electrical energy that passes through the coating into the substrate can be controlled.

With reference again to the invention, the thickness of the conductive coating on some preferred embodiments of the inventive instrument (e.g., thickness D of coating 42 of instrument 12 of FIG. 2) is of the same order of magnitude as the "skin depth" of the coating material at the frequency of the RF field in the MRI system in which the instrument is to be used. In some embodiments of the invention, the thickness of the conductive coating on the instrument body is slightly greater than the "skin depth" of the coating material. In other embodiments, the thickness of the conductive coating on the instrument body is less than the "skin depth" of the coating material. As explained above, the optimal coating thickness is preferably determined empirically, since what constitutes acceptable "positive visibility" of the instrument in an MR image (and what constitutes maximum acceptable distortion or obscuring of an image of a target in the same MR image, due to presence of an image of the instrument) is a subjective judgment that can be made efficiently by a human observer.

As is apparent from the skin depth equation set forth above, the properties $\mu$ and $\sigma$ of the conductive coating material will also affect the preferred coating thickness of the inventive instrument. However, the variation in these properties among most conductive materials is not large. Since the skin depth is a function of the square root of these properties, the selection of the material to be used for the instrument coating will likely be based upon cost considerations (and medical compatibility considerations, where the instrument is used in medical applications).

At this point, a few comments about coating methods are in order. The application of ultra-thin coatings to instruments can be performed by standard techniques (such as those described in Bunshah, Rointan F., et al., *Deposition Technologies for Films and Coatings-Developments and Applications*, Noyes Publications, Park Ridge, N.J., 1982) which are widely used in the electronics industry. In general, there are two principle classes of coating methodologies: (1) those involving droplet formation, transfer and deposition such as plasma spraying, arc spraying, wire explosion spraying, etc., and (2) those involving an atom by atom transfer mode such as physical vapor deposition (PVD) processes of evaporation, ion plating and sputtering, chemical vapor deposition (CVD) and electro-deposition. The chief disadvantage of the droplet transfer process is the porosity in the final coating. Atom by atom methods provide coatings that are not only more uniform and free of porosity, but because they involve deposition of layers of atoms, have thickness and uniformity that can be precisely controlled.

In general any deposition process involves three steps:
(1) Synthesis of the material to be deposited by transition from a solid or liquid phase to a vapor phase;
(2) Transport of the vapors from the material source to the substrate to be coated; and
(3) Condensation of vapors onto the substrate by film nucleation and growth.

Within the PVD processes, sputter coating is an extremely flexible process in that almost any material can be used as a coating and the resulting coatings can be carefully controlled as to thickness, layering of different materials and even patterned using standard masking techniques developed within the electronics industry. Sputter coating can be done in relatively large vacuum chambers making it amenable to relatively high volume production for small components. It is because of this flexibility and production potential that PVD could be used for the ultra-thin coatings described herein.

Another aspect of the invention is a magnetic resonance imaging method including the steps of positioning both a target and an embodiment of the inventive coated instrument in the imaging region of an MRI system, and operating the MRI system to produce an MR image showing both the target and the instrument. It is within the scope of the invention to employ any embodiment of the inventive coated instrument in performing such a method.

Various modifications and variations of the described embodiments of the invention will be apparent to those skilled in the art without departing from the scope and spirit of the invention. Although the invention has been described in connection with specific preferred embodiments, it should be understood that the invention as claimed should not be unduly limited to such specific embodiments.

What is claimed is:

1. A magnetic resonance imaging system, including:

an imaging region and a means for generating a magnetic resonance image of a target object in the imaging region, said magnetic resonance image including an image of the target object, wherein the means for generating the magnetic resonance image includes means for producing an RF field having an RF frequency in the imaging region; and an instrument for use with the target object in the imaging region, said instrument including:

an electrically non-conductive body, sized for use with the target object in the imaging region; and an electrically conductive, ultra-thin coating on at least part of the body, the coating being sufficiently thick to cause the instrument to be positively shown in the magnetic resonance image in response to presence of the instrument in the imaging region with the target object during generation of the magnetic resonance image, wherein the coating consists of material having a skin depth with respect to said RF frequency and the coating has a thickness less than the skin depth.

2. The system of claim 1, wherein the coating is composed of a non-ferromagnetic metal.

3. The system of claim 1, wherein the coating is composed of a ferromagnetic material.

4. The system of claim 1, wherein the coating has a thickness, and the thickness is sufficiently small to avoid significant degrading of the image of the target object during generation of the magnetic resonance image with the instrument and the target object in the imaging region.

5. The system of claim 1, wherein the coating is a non-ferromagnetic metal having a thickness at least substantially equal to 2000 Angstroms.

6. The system of claim 1, wherein the coating covers substantially all of the body.

7. The system of claim 6, wherein the coating is composed of a non-ferromagnetic metal.

8. The system of claim 6, wherein the coating is composed of a ferromagnetic material.

9. The system of claim 6, wherein the coating has a thickness, and the thickness is sufficiently small to avoid significant degrading of the image of the target object during generation of the magnetic resonance image with the instrument and the target object in the imaging region.

10. The system of claim 6, wherein the coating is a non-ferromagnetic metal having a thickness at least substantially equal to 2000 Angstroms.

11. The system of claim 1, wherein the coating covers only a portion or feature of the instrument.

12. The system of claim 1, wherein the coating covers a patterned region of the body.

13. A method for operating a magnetic resonance imaging system, wherein the system includes an imaging region and a means for producing a magnetic resonance image of a target object in the imaging region, said magnetic resonance image including a representation of the target object, wherein the means for generating the magnetic resonance image includes a means for producing an RF field having an RF frequency in the imaging region, said method including the steps of:

(a) positioning an instrument adjacent to or within said target object in the imaging region, where the instrument has a non-electrically conductive body and an electrically conductive, ultra-thin coating on at least part of the body, wherein the coating consists of material having a skin depth with respect to the RF frequency, and the coating has a thickness less than the skin depth; and (b) operating the system to produce a magnetic resonance image showing both the target object and the coated instrument.

14. The method of claim 13, wherein the magnetic resonance image includes a positively shown representation of the instrument.

15. The method of claim 14, wherein the positively shown representation of the instrument does not significantly degrade the representation of the target object.

16. A method for determining an optimal coating thickness for an instrument for use with a magnetic resonance imaging system, wherein the system includes an imaging region and a means for producing a magnetic resonance image of a target object in the imaging region, and wherein the instrument has an electrically non-conductive body and an electrically conductive coating on at least part of the body, the method including the steps of:

(a) positioning a test instrument in the imaging region, said test instrument having an electrically non-conductive test body substantially identical to the electrically non-conductive body, and a test coating of electrically conductive material having a first test thickness on at least part of the test body;

(b) operating the system to produce a test magnetic resonance image showing the test instrument;

(c) positioning at least one additional test instrument in the imaging region, wherein each said additional test instrument has an electrically non-conductive test body substantially identical to the electrically non-conductive body, wherein at least a portion of the test body of each said additional test instrument is coated with a different thickness of said electrically conductive material, wherein each said different thickness differs from the first test thickness, and wherein said first test thickness and each said different thickness together comprise a set of test thicknesses, and said test instrument and said at least one additional test instrument together comprise a set of test instruments;

(d) operating the system to produce at least one additional test magnetic resonance image showing each said additional test instrument, wherein said at least one additional test magnetic resonance image and said test magnetic resonance image together comprise a set of test images; and (e) identifying as the optimal coating thickness, the test thickness which results in a test image having a desired positively shown representation of one of the test instruments.

17. The method of claim 16, wherein the target object is positioned in the imaging region with the test instrument during each of steps (a)–(d), wherein each of the test images includes a representation of the target object, and wherein said desired positively shown representation of one of the test instruments does not significantly degrade the representation of the target object.

* * * * *